United States Patent [19]

Poulsen et al.

[11] 4,206,285
[45] Jun. 3, 1980

[54] SACCHARIFICATION OF ENRICHED FRUCTOSE CONTENT SYRUPS

[75] Inventors: Poul Børge R. Poulsen; Susanne Rugh, both of Vaerløse; Barrie E. Norman, Farum, all of Denmark

[73] Assignee: Novo Industri A/S, Denmark

[21] Appl. No.: 865,077

[22] Filed: Dec. 27, 1977

[51] Int. Cl.$^2$ ............................................. C12P 19/24
[52] U.S. Cl. ...................................... 435/96; 435/94; 435/803; 435/813
[58] Field of Search ................... 195/31 R, 31 F, 115; 536/1; 127/46; 435/94, 96, 99, 803, 813

[56] References Cited

U.S. PATENT DOCUMENTS

| | | |
|---|---|---|
| 3,305,395 | 2/1967 | Scallet et al. ................... 195/31 F X |
| 3,935,070 | 1/1976 | Suekane et al. ..................... 195/31 F |
| 4,011,137 | 3/1977 | Thompson et al. ................ 195/31 R |
| 4,096,036 | 6/1978 | Liu et al. ............................ 195/31 F |

FOREIGN PATENT DOCUMENTS 48-22643  3/1973  Japan ...................................... 195/31 F

OTHER PUBLICATIONS

Nakamura, et al., "Back Polymerization by Saccharifying Amylase", *International Chem. Eng.*, vol. 4, No. 3, pp. 530–534.

*Primary Examiner*—Thomas G. Wiseman
*Attorney, Agent, or Firm*—Fidelman, Wolffe & Waldron

[57] ABSTRACT

Saccharification of low DP polysaccharides in syrups of high fructose content and low glucose content by short term contact with amyloglucosidase e.g. in less than 60 minutes, 1–10 AG units/gm of syrup solids, and syrup concentrations of 2–50 w/o solids in a continuous process employing immobilized AMG.

Suitable high fructose content low glucose syrups are products that result from fractionation of isosyrup into enriched 50+% d.s.b. fructose syrups.

2 Claims, 1 Drawing Figure

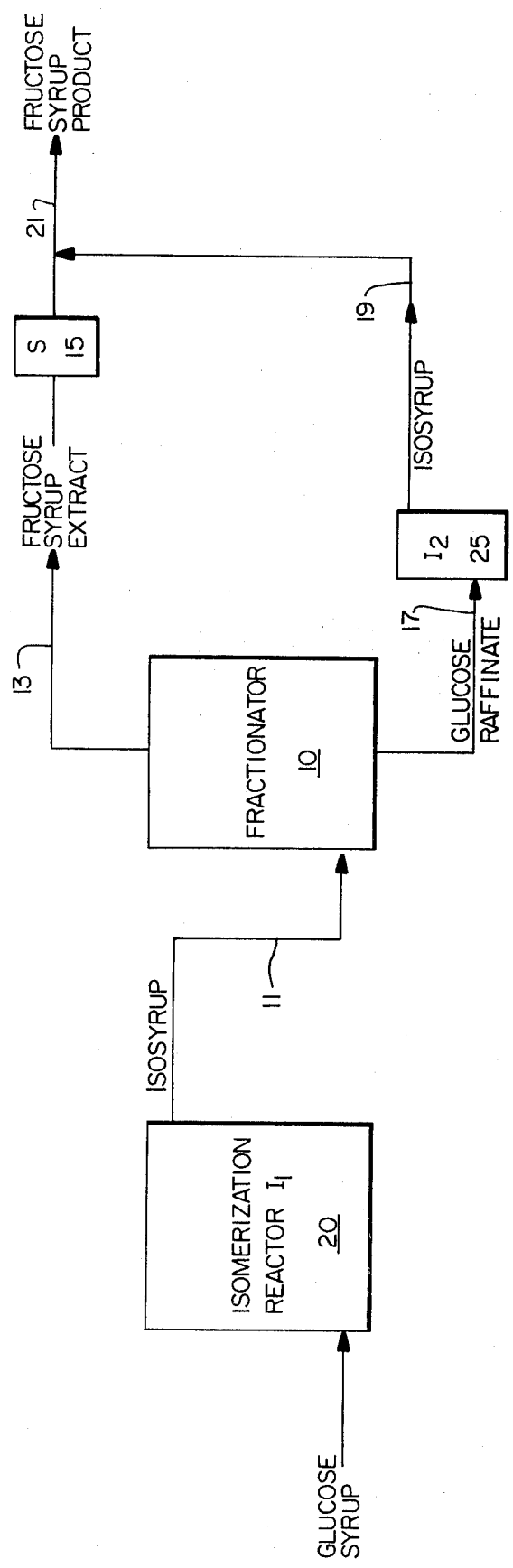

SACCHARIFICATION OF ENRICHED FRUCTOSE CONTENT SYRUPS

This invention relates to a process for reducing the polysaccharide content of enriched fructose syrups.

The carbohydrates available for large scale (food) use as sweetener materials are sucrose, glucose (or dextrose) and a glucose/fructose mixture known in the art as isosyrup. Sucrose, i.e. cane and beet sugar, is the standard sweetener of commerce and to a very large extent its price level determines the market penetration of glucose and isosyrup into the sweetener market. However, price considerations may not be the controlling factor, as witness the usual situation wherein glucose is cheaper than isosyrup, and isosyrup is cheaper than sucrose yet the sweetener market employs more sucrose than isosyrup, and more isosyrup than glucose.

The sweetness factor must be taken into account. Glucose is less sweet than sucrose. Fructose, however, is sweeter than sucrose. Unfortunately, the enzymatic isomerization procedures employed to convert glucose into isosyrup can not exceed about 45% fructose d.s.b. (dry solids basis). A syrup enriched in fructose to more than 50% fructose d.s.b. is required to overcome the sweetness factor consideration.

An inexpensive fructose/glucose syrup with 55% fructose d.s.b., purportedly would have wide acceptance, in substitution for sucrose (for uses that do not accept the 42% fructose content isosyrup of commerce).

Fructose contents in excess of 50% d.s.b. can be achieved by application of adsorptive separation techniques to isosyrup separating the isosyrup into an enriched fructose fraction and a glucose fraction. For convenience the enriched in fructose fraction is hereinafter called the extract, and the enriched in glucose fraction is hereinafter termed the raffinate. Also for convenience, the term enriched fructose syrup is herein employed to denote syrups having in excess of 50% d.s.b. fructose therein. The isosyrup of commerce contains a significant polysaccharide content, e.g. 7%. The polysaccharides can be concentrated in either the fructose extract or the glucose raffinate. Conversely, either the fructose extract or the glucose raffinate can be made almost pure monosaccharides i.e. DX-98 and higher.

In copending application Ser. No. 851,709 it was assumed that the polysaccharides concentrated only in the glucose raffinate. It has since been discovered that the separation may readily produce an essentially pure in monosaccharide glucose raffinate, with essentially all the polysaccharides appearing in the fructose extract.

THE INVENTION

Briefly stated the present invention involves a multi-step process wherein a fructose-glucose syrup is fractionated into a fructose/polysaccharide extract and a glucose raffinate, and then the extract is saccharified to DE-98 or higher. Optionally thereafter the raffinate is isomerized into a fructose-glucose syrup (i.e. isosyrup). If desired the isomerized raffinate is added to the fructose extract, whereby only one product results, namely an enriched in fructose 50+% fructose product which is higher in DE and in DX than the isosyrup starting material. (The term DX includes here both fructose and glucose).

An important aspect of this invention is a continuous procedure for saccharification of the fructose/polysaccharide extract. It has been found that the purity level of the enriched fructose syrup product can be substantially increased by separating an isosyrup into a pure in monosaccharide glucose raffinate and an impure but enriched in fructose extract, then saccharifying the fructose extract to a 98+DE syrup.

The process results in an enriched fructose syrup product having a monosaccharide content of at least about 98 DX.

RATIONALE OF THE INVENTION

The isosyrup of commerce normally is described to the trade in terms of its fructose content (42% fructose). The significant presence of polysaccharides therein are acknowledged but inferentially by provision of the dextrose equivalent, (e.g. DE 96) of the syrup. The polysaccharide content of a DE 96 syrup is about 7 w/o d.s.b. Since polysaccharides constitute a sweetner reducing and taste impairing impurity, their presence constitutes a detriment in the isosyrup (to the sales value, at least), and would be a detriment in enriched fructose syrups.

Fractionation of isosyrup is capable of concentrating the polysaccharide content into either fraction, i.e. either in the glucose raffinate or the fructose extract. The split will, of course, raise the polysaccharide content of that fraction in proportion to the split, between extract and raffinate. If concentration of the polysaccharide content of an isosyrup in one particular fraction were somehow found to be the more desirable, then their (inherent) concentration therein would be an asset to the fructose/glucose separation system as a whole.

As pointed out in copending application Ser. No. 851,709 filed Nov. 15, 1977 concentration of the polysaccharides in the glucose raffinate is advantageous, because increased concentration thereof makes the polysaccharides more amenable for saccharification to glucose. A polysaccharide containing glucose raffinate fraction from an isosyrup fractionation system can be saccharified into a glucose product of higher purity than the DE-96 of the isosyrup. Concentration of the polysaccharides into the fructose extract is even more advantageous, because saccharification of a fructose/polysaccharide mixture proceeds almost to completion. A DE exceeding 98 can be obtained routinely. In contrast saccharification of a comparable glucose/polysaccharide mixture to a DE in excess of 96 is quite difficult requiring close control over the saccharifying procedure.

According to practice of this invention an isosyrup is (adsorptively) fractionated into an enriched fructose/polysaccharide extract fraction and an essentially pure in monosaccharide glucose raffinate fraction, and thereafter the enriched fructose extract is saccharified to a dextrose equivalent DE 98 and higher. DE-98 is much purer than the DE of the isosyrup starting material. By concentrating the polysaccharides in the fructose extract fraction, then saccharifying this fraction the ultimate enriched fructose syrup will have a monosaccharide content at least about 98 DX.

Basically the limiting criteria imposed upon practice of this invention are the criteria set by the fractionation yet, per se, the separation of an isosyrup into an enriched fructose extract and a glucose raffinate form no part of this invention. Several modes of fractionation have been proposed to the art, e.g. the "Sorbex" system by U.O.P. Inc. Suffice it here to say that adsorption fractionation of an isosyrup into a fructose/polysaccharide extract and a pure in monosaccharide glucose raffinate can be carried out by known to the art techniques and that the details of such fractionation form no part of this invention.

Batch saccharification of dextrins into high DE syrups are well known to the art and enzymatic saccharification is contemplated herein using the enzymes, pH, syrup solids concentrations and temperature ranges long established for saccharification of dextrins. However, the continuous saccharification procedures disclosed in copending Ser. No. 810,788 filed June 28, 1977, U.S. Pat. No. 4,116,771, are particularly well suited for saccharifying a fructose/polysaccharide extract to a high DE syrup.

Specifically the polysaccharides in the fructose/polysaccharide extract are low molecular weight, being very largely di-and tri-saccharides, which saccharify quickly. The saccharifying enzymes available to the art to catalyse hydrolysis of polysaccharides into glucose are known to catalyse glucose dimerization into maltose and iso-maltose. Fortunately, saccharification of polysaccharides into glucose proceeds quicker than the reversionary formation of isomaltose. In the instance of an enriched fructose extract fraction, the fructose content will exceed 50% d.s.b. The glucose content normally will not exceed 25% d.s.b. even after saccharification. The fructose has been found to be inert to the enzyme (in the saccharification system), and therefore the glucose reversion reaction is not at all favored vis a vis the saccharification reaction. As a result very little maltose and isomaltose are formed as the saccharification proceeds to virtual completion. In summary the continuous saccharification herein contemplated is saccharification of a fructose syrup containing at least about 5% by weight d.s.b. of polysaccharides and less than about 15% by weight d.s.b. of glucose to a syrup of DE 98 higher. The syrup solids content may vary widely, 2–50 w/o solids content. Therefore saccharification of an enriched fructose syrup can be carried out under circumstances that would not be recommended for either a dextrin or for a high glucose content syrup (because of the reversion reaction).

Although continuous saccharification is preferred, batch saccharification is herein contemplated as well. Batch saccharification of a fructose polysaccharide extract may be carried out rapidly e.g. with from 1–10 AG units/gm of syrup solids, for 1–10 hours. The syrup concentration is not critical e.g. 2–50% w/o solids. The reaction temperatures range and pH range are the same as for saccharifying dextrins and even may be broader, i.e. 55°–60° C., pH 3.5–5.0.

As has been indicated above particularly preferred is the continuous saccharifying method with an immobilized Amyloglucosidase (AMG), reference being made to copending application Ser. No. 810,788 for disclosure of an immobilized AMG suitable for practice of this invention. The high AMG concentrations and short time contact period of continuous saccharification are well suited to saccharifying fructose/polysaccharide extracts.

The continuous saccharification of a fructose-polysaccharide extract is preferably conducted at a flow rate corresponding to 1 gm of dry syrup solids per gm of enzyme per hour (i.e. a contact time of 1–60 minutes). The enzyme activity is in the range of 1–30 AG units per gram. The syrup concentration may vary from 2–50 w/o (d.s.b.). Typical temperature and pH conditions in the column are in the range of 50°–60° C. and pH 3.5–7.0, respectively.

DETAILED PRACTICE OF THE INVENTION

For further understanding of this invention, reference is now made to the attached drawing wherein the single FIGURE illustrates the process of this invention in block form. The drawing also illustrates (in block form) how the process of this invention interfits with the conversion of glucose syrups into isosyrup.

Referring now to the drawing, it may be seen that fractionator 10 receives an iso-syrup feed from line 11 and discharges a fructose extract into line 13, and a high in monosaccharide purity glucose raffinate into line 17. The fructose content of the isosyrup feed from isomerization reactor 20 will not exceed about 45%, and for exemplary purposes the commercial quality isosyrup of 42% fructose, 51.3% glucose and 6% polysaccharides may be considered typical of the available fructose/glucose syrups.

The details of the fractionator 10 are not illustrated. As has already been pointed out the fractionation per se forms no part of this invention. Several modes of fructose separation systems are known to the art, with at least one offered on a commercial basis (i.e. "Sorbex" by UOP). Suffice it then to say only that fractionator 10 operates on adsorption principles, and separates the feed stream iso-syrup into an enriched fructose/polysaccharide extract having more than 50% fructose d.s.b. The fructose content of the extract can be predetermined as desired (since such flexibility is one attribute of this invention), but for exemplary purposes will be illustrated at 85% fructose d.s.b. For illustrative purposes the ultimate fructose content of the enriched fructose syrup product made according to practice of this invention will be 55% fructose d.s.b.

The saccharifier 15 into which the extract fructose/polysaccharide stream flows by way of line 13 may be either a batch process or a continuous immobilized enzyme column operated as has been described above and is exemplified hereafter. In either event the saccharifier 15 is adapted to convert the polysaccharide content of the extract into a 98 DE+ syrup as quickly as is reasonably possible. The saccharified extract from saccharifier 15 leaves the system by way of line 21, as is illustrated in the drawing.

The raffinate leaving separator 10 by way of line 17 may be passed to isomerizer 25 and then after isomerization the raffinate (now for example an isosyrup of about ⅓ fructose ⅔ glucose) is passed by way of line 19 for addition to the saccharified fructose extract in line 21 to adjust the fructose concentration downward. Since, the raffinate is isomerized into an iso-syrup of purity essentially equal to the 99+DE of the glucose raffinate a DE 98 or higher enriched fructose product results from the admixture.

For further understanding of this invention conversion of a typical iso-syrup into a 55% fructose syrup will be illustrated with fractionation conditions (Sorbex system) productive of 85% fructose d.s.b. (The isosyrup feed contains 42% fructose, 53% glucose, 1.5% maltose/maltulose, 1.5% isomaltose and 2% DP3+d.s.b.

1. 1000 Pounds/hr d.s.b. of iso-syrup solids from isomerizer 20 is fractionated in fractionator 10 into 427 lbs/hr of an extract containing 85% fructose and 3.3% glucose 3.5% maltose, 3.5% isomaltose, 4.7% DP-3+ and 573 lbs/hr of a raffinate containing 90% glucose, 10% fructose 0.1% polysaccharides.

Saccharification of this enriched fructose extract fraction in saccharifier 15 results in a syrup containing 0.2% maltose/maltulose, 3.5% isomaltose, 0.4% DP3+, 85% fructose and 11.1% glucose. Isomerization of the glucose raffinate fraction in isomerizer 25 produces an iso-syrup of 32.7% fructose, 67.3% glucose and 0.1% polysaccharides. The two fractions are now reunited in line 21, resulting in a 98.3 DX (99 DE) product of the following composition 55% fructose, 43.3% glucose and 0.1% maltose, 1.5% isomaltose and 0.1% DP-3+ polysaccharides. It may be noted that this 55% fructose enriched fructose product is of much greater purity than the isosyrup feed stream. Moreover, a high isomaltose content isosyrup feed stream has been exemplified. Many isosyrups of commerce have an isomaltose content of below 1%.

If a product with a fructose content of more than about 65% is desired (without production of a glucose co-product) the isosyrup from isomerizer 25 can be recycled back into the fractionator 10.

For further understanding of this invention reference is now made to the following specific examples.

EXAMPLE I

Comparison between Saccharification of Fructose-Extract by Soluble AMG and by Immobilized AMG The saccharification of a fructose extract consisting of 10.0% Glucose, 78% Fructose, 8.6% Maltose, 0% Isomaltose and 3.5% Maltotriose and higher polymers was performed in a batch operation under the following conditions:

28.1 w/w% dry solid
60° C., pH 4.5
The following experimental results were obtained:

| | 5000 ml batch 20 ml AMG 150 | | | |
|---|---|---|---|---|
| Time, hours | Monosacc. | Maltose | Isomaltose | DP3+ |
| 0 | 87.9 | 8.6 | 0.0 | 3.5 |
| 0.17 | 93.2 | 4.1 | 0.0 | 2.7 |
| 0.50 | 95.3 | 2.2 | 0.2 | 2.3 |
| 1.00 | 97.8 | 0.7 | 0.1 | 1.4 |
| 2.00 | 99.4 | 0.4 | 0.1 | 0.1 |
| 4.00 | 99.4 | 0.2 | 0.2 | 0.2 |
| 24.00 | 99.2 | 0.2 | 0.4 | 0.2 |

At the conclusion of saccharification the glucose content was 21.5% d.s.b; fructose content remained at 78%.

A fructose-extract with the same composition was saccharified in a fixed bed column operation.

The IAMG was produced according to example 2 in patent application Ser. No. 810,788 filed June 28, 1977. The following conditions were applied:

28.1 w/w% dry solid
55° C., pH 4.5
Column size: 2.5 cm (d) by 25 cm (h)
Amount of IAMG: 10 g
Inlet extract composition: as above

| | | Product Composition % | | | |
|---|---|---|---|---|---|
| Space Time | Flow ml/h | Mono sacc | Maltose | Iso- malt | DP3+ |
| 5 minutes | 370 | 97.5 | 1.5 | 0.0 | 1.0 |
| 6.5 | — | 279 | 98.0 | 1.2 | 0.0 | 0.8 |
| 11 | — | 144 | 99.1 | 0.7 | 0.0 | 0.2 |
| 14 | — | 129 | 99.3 | 0.4 | 0.1 | 0.2 |
| 23 | — | 78 | 99.5 | 0.2 | 0.1 | 0.2 |

The product composition was determined by HPLC.
The 11 minute product contained 21.2% Glucose d.s.b; the fructose content remained at 78% d.s.b.

EXAMPLE II

Long Time Saccharification of Fructose-Extract by IAMG

The saccharification of a fructose-extract consisting of 77.1% Fructose, 10.6% Glucose, 7.8% Maltose, 1.1% Isomaltose and 3.4% Maltotriose and higher polymers was carried out in a fixed bed column of IAMG under the following conditions:

28.3 w/w% dry solid
55° C., pH 4.5
Column size: 2.5 cm (d) by 25 cm (h)
Amount of IAMG: 10 g
Constant flow rate 160 ml/h
Contact time 11 minutes

| | Product Composition % | | | |
|---|---|---|---|---|
| Time, days | Mono sacc | Mal- tose | Iso- malt | DP3+ |
| 1 | 98.4 | 0.3 | 1.1 | 0.2 |
| 3 | 98.0 | 0.6 | 1.1 | 0.3 |
| 6 | 97.5 | 0.9 | 1.1 | 0.5 |
| 10 | 97.1 | 1.3 | 1.1 | 0.5 |
| 15 | 96.9 | 1.4 | 1.1 | 0.6 |
| 20 | 96.5 | 1.5 | 1.1 | 0.9 |

Even after 20 days the product contained 77.1% fructose, 19.4% glucose and only 3.5% polysaccharides.

EXAMPLE III

| Comparison between Saccharification of Fructose/Poly-Saccharide Extract and a Glucose/Polysaccharide Raffinate by Immobilized AMG* | | | | | | | | | | |
|---|---|---|---|---|---|---|---|---|---|---|
| Glucose/Polysaccharide Raffinate | | | | | Fructose/Polysaccharide Extract | | | | | |
| 84.3% Glucose | | | | | 2.9% Glucose | | | | | |
| 2.9% Fructose | | | | | 84.3% Fructose | | | | | |
| 9.4% Maltose | | | | | 9.4% Maltose | | | | | |
| 0.5% Isomaltose | | | | | 0.5% Isomaltose | | | | | |
| 2.9% Maltotriose + | | | | | 2.9% Maltotriose + | | | | | |
| Space time | Flow | DX | M | IM | DP3+ | Space time | Flow | DX | M | IM | DP3+ |
| 4.7min | 181 | 96.4 | 1.2 | 0.6 | 1.8 | 4.7 | 181 | 97.0 | 1.6 | 0.5 | 0.9 |
| 7.5 | 113 | 97.2 | 1.0 | 0.6 | 1.2 | 7.5 | 113 | 98.0 | 1.0 | 0.5 | 0.5 |
| 10.0 | 85 | 97.8 | 0.8 | 0.8 | 0.6 | 10.0 | 85 | 98.5 | 0.7 | 0.5 | 0.3 |
| 20.0 | 43 | 96.9 | 0.7 | 2.0 | 0.4 | 20.0 | 43 | 99.0 | 0.2 | 0.6 | 0.2 |

| | | | | | | | | | | | |
|---|---|---|---|---|---|---|---|---|---|---|---|
| Comparison between Saccharification of Fructose/Poly-Saccharide Extract and a Glucose/Polysaccharide Raffinate by Immobilized AMG* ||||||||||||
| 37.5 | 23 | 93.6 | 1.3 | 4.0 | 1.2 | 37.5 | 23 | 99.1 | 0.1 | 0.6 | 0.2 |

*The IAMG was produced according to example 2 in patent application Serial No. 810,788 filed June 28, 1977. The following conditions were applied: 20.5 w/w% dry solid 55° C. and pH 4.5. The columns were 2.5 cm (d) by 40 cm (h), with 5g of IAMG.

CONCLUSION

Fructose/polysaccharide extract saccharification results in significantly higher DX values than saccharification of a comparable glucose/polysaccharide raffinate.

What is claimed:

1. A continuous process for saccharifying a fructose syrup containing therein in excess of 50% w/w d.s.b. fructose, at least about 5% w/w d.s.b. of dissacharides, trisaccharides and polysaccharides and less than about 25% glucose d.s.b. which comprises treatment of the syrup with an immobilized amyloglucosidase under saccharifying temperature and pH conditions for a total contact time of less than 60 minutes to produce a syrup with a DX of at least 98 and recovering said syrup.

2. The process of claim 1 wherein the syrup concentration is 2–50% by weight solids.

* * * * *